(12) United States Patent
Shimizu et al.

(10) Patent No.: US 9,888,899 B2
(45) Date of Patent: Feb. 13, 2018

(54) X-RAY DIAGNOSTIC APPARATUS

(71) Applicant: Toshiba Medical Systems Corporation, Otawara-shi (JP)

(72) Inventors: Yoshinori Shimizu, Nasushiobara (JP); Manabu Tanaka, Otawara (JP); Teruomi Gunji, Otawara (JP); Takayuki Ishikawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 129 days.

(21) Appl. No.: 14/178,940

(22) Filed: Feb. 12, 2014

(65) Prior Publication Data
US 2014/0169525 A1   Jun. 19, 2014

Related U.S. Application Data

(63) Continuation of application No. PCT/JP2013/074594, filed on Sep. 11, 2013.

(30) Foreign Application Priority Data

Sep. 13, 2012 (JP) ................... 2012-201524

(51) Int. Cl.
*A61B 6/00* (2006.01)
*A61B 6/06* (2006.01)
*A61B 6/12* (2006.01)

(52) U.S. Cl.
CPC ............... *A61B 6/542* (2013.01); *A61B 6/06* (2013.01); *A61B 6/12* (2013.01); *A61B 6/5211* (2013.01);
(Continued)

(58) Field of Classification Search
CPC .................. A61B 6/06; A61B 6/542
See application file for complete search history.

(56) References Cited

U.S. PATENT DOCUMENTS

2004/0066885 A1* 4/2004 Ogawa ................ A61B 6/06
                                                                 378/42
2004/0127789 A1* 7/2004 Ogawa ................ A61B 6/481
                                                                 600/425
(Continued)

FOREIGN PATENT DOCUMENTS

CN        101091817 A     12/2007
JP        8-164130 A       6/1996
(Continued)

OTHER PUBLICATIONS

Combined Chinese Office Action and Search Report dated Aug. 4, 2015 in Patent Application No. 201380001644.6 (with English translation of categories of cited documents).
English translation of the International Search Report dated Oct. 29, 2013, in PCT/JP2013/074594.
International Search Report dated Oct. 29, 2013 in PCT/JP2013/074594 filed Sep. 11, 2013.
(Continued)

*Primary Examiner* — Dani Fox
(74) *Attorney, Agent, or Firm* — Oblon, McClelland, Maier & Neustadt, L.L.P.

(57) ABSTRACT

An X-ray diagnostic apparatus according to one embodiment includes an X-ray generating device, an X-ray detector, an image generation device, a display device, a portion detection device, and an attenuation device. The X-ray generation device generates X-rays to irradiate an object. The X-ray detector detects X-rays transmitted through the object. The image generation device generates an X-ray image based on the detected X-rays. The display device displays the X-ray image. The portion detection device detects an exposure dose reduction target portion based on the X-ray image. The attenuation device attenuates the X-rays to irradiate a region including the detected portion.

4 Claims, 9 Drawing Sheets

(52) U.S. Cl.
CPC ............ *A61B 6/545* (2013.01); *A61B 6/4035* (2013.01); *A61B 6/487* (2013.01)

(56) References Cited

U.S. PATENT DOCUMENTS

| | | | |
|---|---|---|---|
| 2007/0297566 A1 | 12/2007 | Urano et al. | |
| 2007/0297572 A1 | 12/2007 | Moritake et al. | |
| 2008/0152088 A1* | 6/2008 | Wang ...................... | A61B 6/02 378/98.12 |
| 2011/0013742 A1* | 1/2011 | Zaiki ..................... | A61B 6/035 378/15 |
| 2011/0150173 A1 | 6/2011 | Shinno | |
| 2011/0164724 A1* | 7/2011 | Ohta ....................... | A61B 6/06 378/62 |
| 2012/0189093 A1 | 7/2012 | Zaiki et al. | |

FOREIGN PATENT DOCUMENTS

| | | |
|---|---|---|
| JP | 2003-265449 A | 9/2003 |
| JP | 2006-122448 A | 5/2006 |
| JP | 2007-159913 A | 6/2007 |
| JP | 2008-000456 A | 1/2008 |
| JP | 2011-019633 A | 2/2011 |
| JP | 2011-125486 A | 6/2011 |
| JP | 2012-75782 A | 4/2012 |
| WO | WO 2006/088104 A1 | 8/2006 |

OTHER PUBLICATIONS

Written Opinion dated Oct. 29, 2013 in PCT/JP2013/074594 filed Sep. 11, 2013.
Office Action dated Mar. 7, 2017, in Japanese Patent Application No. 2012-201524.

* cited by examiner

X-RAY DIAGNOSTIC APPARATUS

CROSS-REFERENCE TO RELATED APPLICATIONS

This application is based upon and claims the benefit of priority from Japanese Patent Application No. 2012-201524, filed on Sep. 13, 2012; the entire contents of which are incorporated herein by reference.

FIELD

Embodiments described herein relate generally to an X-ray diagnostic apparatus.

BACKGROUND

In recent years, a treatment using a catheter is provided for an aneurysm, or clogging of cerebral blood vessels, under X-ray fluoroscopy by an X-ray diagnostic apparatus in some cases. Such intravascular treatment using a catheter is called IVR (interventional radiology).

On the other hand, the X-ray absorption amount changes depending on the portion of a patient. For example, the absorption amount of a portion such as a crystalline lens (eye) or thyroid is high. The X-ray conditions of IVR are determined to acquire information necessary for a catheter method. That is, the X-ray conditions of IVR do not consider the fact that the absorption amount changes depending on each portion. Under the X-ray conditions which define a long fluoroscopy time, a high sensitivity portion such as an eye or thyroid may be exposed at a high dose.

On the other hand, for an X-ray diagnostic apparatus, there are known a technique of reducing an exposure dose by inserting a compensation filter such as a metal plate into an arbitrary irradiation field to attenuate X-rays, and a technique of preventing exposure by inserting a collimator such as a lead plate into an arbitrary irradiation field to block X-rays.

The above-described X-ray diagnostic apparatus, however, requires manual operation of a compensation filter and collimator. Therefore, the exposure dose of a high sensitivity portion within an X-ray irradiation range is not automatically reduced. In particular, the compensation filter is originally a filter used to prevent halation, and is thus not automatically used to reduce the exposure dose.

It is, however, desirable for the X-ray diagnostic apparatus to automatically reduce the exposure dose of a high sensitivity portion of a patient. In addition to a high sensitivity portion of the patient, it is desirable to reduce the exposure dose of a portion such as the hand of a technician at the time of paracentesis and the hand of an assistant at the time of PPI (Percutaneous Peripheral Intervention). In summary, an X-ray diagnostic apparatus which can automatically reduce the exposure dose of a high sensitivity portion of a patient and that of an exposure dose reduction target portion such as the hand of a technician or assistant is required.

It is an object to provide an X-ray diagnostic apparatus which can automatically reduce the exposure dose of an exposure dose reduction target portion.

DETAILED DESCRIPTION

Figure 1:
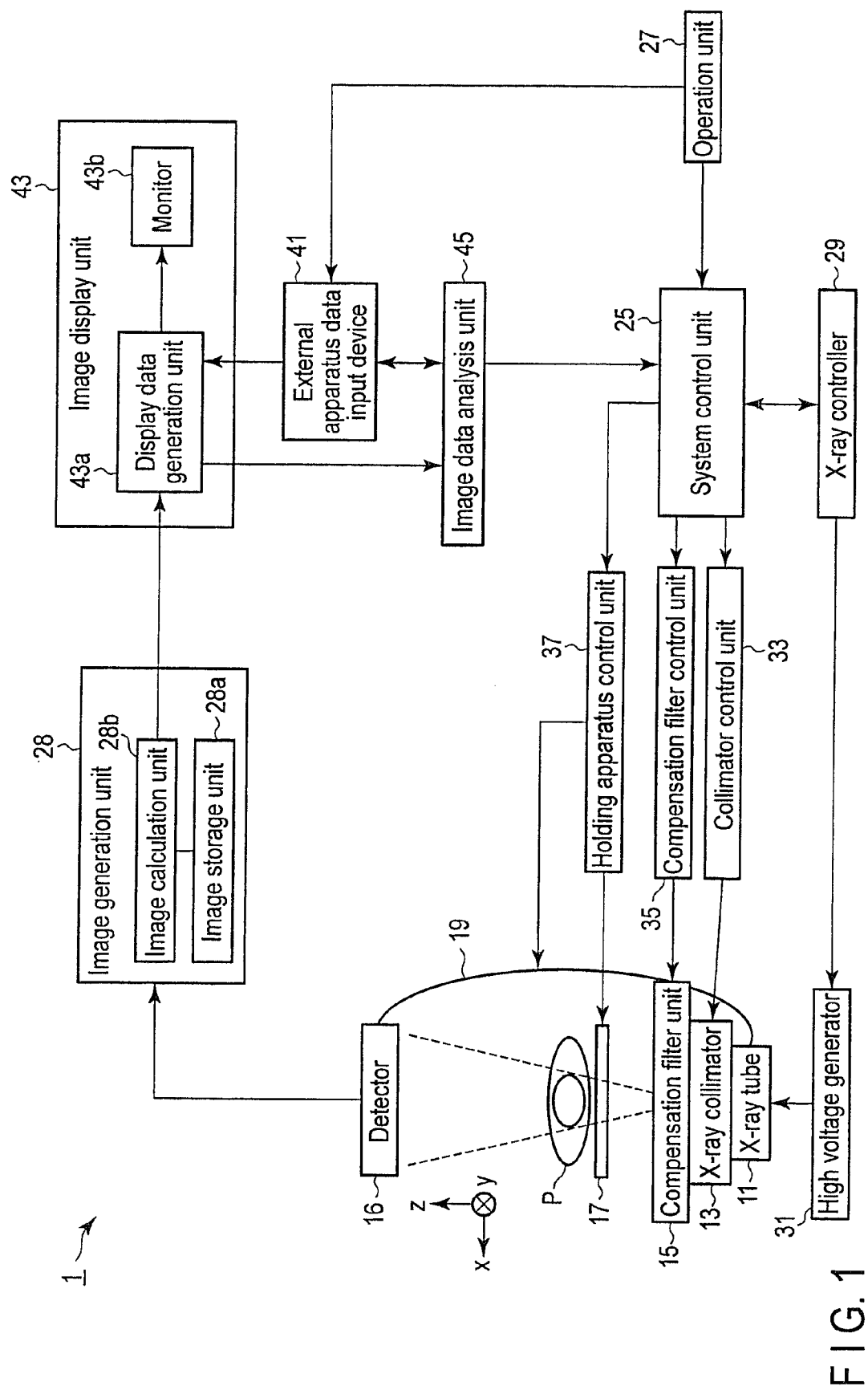
FIG. 1 is a block diagram showing the arrangement of an X-ray diagnostic apparatus according to the first embodiment.

In general, according to one embodiment, an X-ray diagnostic apparatus includes an X-ray generation device, an X-ray detector, an image generation device, a display device, a portion detection device, and an attenuation device.

The X-ray generation device generates X-rays to irradiate an object.

The X-ray detector detects X-rays transmitted through the object.

The image generation device generates an X-ray image based on the detected X-rays.

The display device displays the X-ray image.

The portion detection device detects an exposure dose reduction target portion based on the X-ray image.

The attenuation device attenuates the X-rays to irradiate a region including the detected portion.

Each embodiment will be described below with reference to the accompanying drawings. Note that the same reference numerals denote constituent elements having almost the same functions and arrangements in the following description, and a repetitive description will be made only when necessary.

First Embodiment

FIG. 1 is a block diagram showing the arrangement of an X-ray diagnostic apparatus according to the first embodiment. In the following description, the x direction represents the lateral direction of an object P, the y direction represents the body axis direction of the object P, and the z direction represents the thickness direction of the object P.

An X-ray diagnostic apparatus 1 includes, as a data acquisition system, an X-ray tube 11, an X-ray collimator 13, a compensation filter unit 15, an X-ray detector 16, a bed 17, and a C-arm 19. The C-arm 19 is used to arrange the X-ray tube 11 and the X-ray detector 16 to face each other. The X-ray diagnostic apparatus 1 includes, as a data processing system, a system control unit 25, an operation unit 27, an image generation unit 28, an X-ray controller 29, a high voltage generator 31, a collimator control unit 33, a compensation filter control unit 35, a holding apparatus control unit 37, an external apparatus data input device 41, an image display unit 43, and an image data analysis unit 45.

The X-ray tube 11 is a vacuum tube which generates X-rays. The X-ray tube 11 generates X-rays by accelerating electrons with a high voltage generated by the high voltage generator 31 and bombarding them against a target.

The bed 17 has a mechanism which can tilt it up/down and perform a positioning operation while the object P lies on it.

Figure 2:
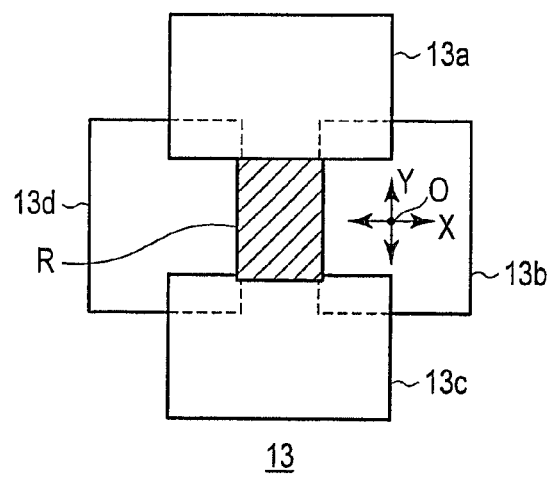
FIG. 2 is a plan view for explaining collimator blades according to the first embodiment.

The X-ray collimator 13 is provided between the X-ray tube 11 and the object P, and serves as a collimator apparatus for forming an X-ray irradiation region R on the detection surface of the X-ray detector 16 and preventing the object P from unnecessarily being exposed to X-rays. The X-ray collimator 13 includes a plurality of X-ray collimator blades 13a to 13d which can independently move to limit the irradiation region R of X-rays on the object P to a region of interest (see FIG. 2). Referring to FIG. 2, the x and y directions in which each of the X-ray collimator blades 13a to 13d can move are orthogonal to the X-ray irradiation direction. Each of the X-ray collimator blades 13a to 13d is formed by lead or the like to block X-rays. Note that the image data analysis unit 45 sets the region of interest as a region including a predetermined instrument projected on an X-ray image.

Figure 3:
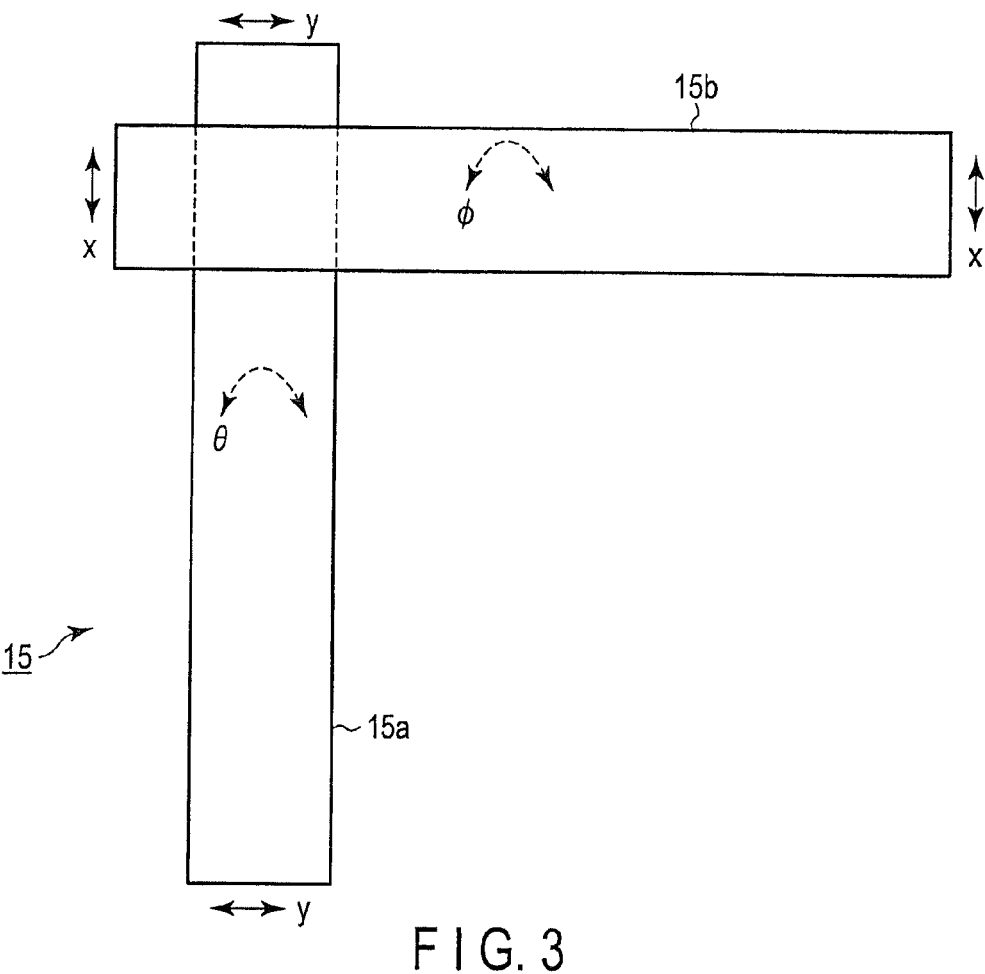
FIG. 3 is a plan view for explaining compensation filters according to the first embodiment.

The compensation filter unit 15 is a filter which is provided between the X-ray collimator 13 and the object P and attenuates X-rays that irradiate an exposure dose reduction target portion, and includes a plurality of compensation filters 15a and 15b which can individually move (see FIG. 3). Each of the compensation filters 15a and 15b is formed by, for example, a metal plate having a rectangular shape. In the initial state, for example, the compensation filters 15a and 15b are arranged so that their longitudinal directions are orthogonal to each other. Each of the compensation filters 15a and 15b can be translated in the x or y direction by moving its ends by equal distances, and can be rotated in the $\theta$ or $\varphi$ direction by moving its ends by different distances. Referring to FIG. 3, the x, y, $\theta$, or $\varphi$ direction in which each of the compensation filters 15a and 15b can move is perpendicular to the X-ray irradiation direction. The number of such compensation filters 15a and 15b is not limited to two, and may be one or larger than two.

The X-ray detector 16 is a flat panel detector (FPD) provided so that its detection surface faces the X-ray tube 11 through the bed 17. The FPD includes, for example, a scintillator and a photodiode array. The FPD generates electrons/holes by causing X-rays transmitted through the object P to strike a photoelectric film, accumulates the electrons/holes in a semiconductor switch, and reads them out as an electrical signal, thereby detecting an X-ray signal.

The bed 17 has a mechanism which can tilt it up/down and perform a positioning operation while the object P lies on it.

The system control unit 25 serves as a central processing apparatus which controls acquisition of image data and controls image processing, image reproduction processing, and the like for acquired image data.

The operation unit 27 includes a keyboard, a mouse, buttons, and an operation lever for inputting an instruction to set, change, or move the X-ray irradiation region R or exposure dose reduction region, or designation of a high sensitivity portion. The exposure dose reduction region indicates a region on the detection surface of the X-ray detector 16, in which the compensation filters 15a and 15b attenuate X-rays.

The image generation unit 28 generates an X-ray image (non-contrast image, contrast image, and difference image) based on the X-ray data obtained by the X-ray detector 16. The non-contrast image is an X-ray image before a radiopaque dye is injected, and is a projection image including a bone image. The contrast image is an X-ray image after the radiopaque dye is injected, and is a projection image including bone and blood vessel images. The difference image is an X-ray image representing the difference between the contrast image and the non-contrast image, and is a projection image including a blood vessel image. For example, the difference image can be generated when an image calculation unit 28b calculates the difference between the non-contrast image stored in an image storage unit 28a and the contrast image based on the X-ray data obtained by the X-ray detector 16.

The X-ray controller 29 controls the high voltage generator 31 which generates a high voltage to be applied to the X-ray tube 11.

The high voltage generator 31 generates a high voltage based on a control signal supplied by the X-ray controller 29, and supplies the high voltage to the X-ray tube 11.

The collimator control unit 33 controls the movement of the X-ray collimator blades 13a to 13d to set, move, or change the X-ray irradiation region R. The collimator control unit 33 controls the movement of each of the X-ray collimator blades 13a to 13d so as to, for example, shield a portion detected by the image data analysis unit 45 from X-rays while irradiating the region of interest set by the image data analysis unit 45 with the X-rays. At this time, the X-ray collimator blades 13a to 13d and the collimator control unit 33 constitute an attenuation device for attenuating X-rays to irradiate a region including the portion detected by the image data analysis unit 45. Note that the embodiment is not limited to this. The X-ray collimator blades 13a to 13d may constitute an attenuation device and the collimator control unit 33 may constitute a control unit for controlling the movement of the attenuation device for attenuating X-rays to irradiate a portion when the image data analysis unit 45 detects this portion.

The compensation filter control unit 35 controls the movement of the compensation filters 15a and 15b to set, change, or move the exposure dose reduction region. The compensation filter control unit 35 controls the movement of the compensation filters 15a and 15b to, for example, shield the portion detected by the image data analysis unit 45 from X-rays. At this time, the compensation filters 15a and 15b and the compensation filter control unit 35 constitute an attenuation device for attenuating X-rays to irradiate a region including the portion detected by the image data analysis unit 45. Note that the embodiment is not limited to this. The compensation filters 15a and 15b may constitute an attenuation device and the compensation filter control unit 35 may constitute a control unit for controlling the movement of the attenuation device for attenuating X-rays to irradiate a portion when the image data analysis unit 45 detects this portion.

The holding apparatus control unit 37 controls the top of the bed 17 in accordance with an instruction from the system control unit 25.

An X-ray detector control unit controls the operation of the X-ray detector 16.

The external apparatus data input device 41 can use an apparatus which provides a CT image or a 3D workstation, as needed. For example, the external apparatus data input device 41 sends a CT image to a display data generation unit 43a, and sends a template image to the image data analysis unit 45. The CT image is an image obtained by imaging the object P by a CT apparatus (not shown). The template image is a three-dimensional image of a phantom including a bone and blood vessel images, or a projection image of the whole body for each representative angle.

The image display unit 43 displays the X-ray image generated by the image generation unit 28. More specifically, the image display unit 43 includes the display data generation unit 43*a* and a monitor 43*b*.

The display data generation unit 43*a* generates display data including at least the X-ray image generated by the image generation unit 28, and sends the display data to the monitor 43*b*. Note that when there is a CT image sent by the external apparatus data input device 41, the display data includes the CT image and the X-ray image generated by the image generation unit 28. That is, it is essential to display the X-ray image generated by the image generation unit 28 but it is not essential to display a CT image from another apparatus.

The monitor 43*b* displays the display data received from the display data generation unit 43*a*.

The image data analysis unit (portion detection device) 45 detects an exposure dose reduction target portion based on the X-ray image generated by the image generation unit 28. For example, the image data analysis unit 45 may include a storage unit (not shown) for storing a template image including an exposure dose reduction target portion, and detect the exposure dose reduction target portion in the X-ray image by comparing the template image with the X-ray image. Furthermore, the image display unit 43 may display an X-ray image almost immediately before the collimator control unit 33 or the compensation filter control unit 35 controls the movement, at a location indicating a region including the portion detected by the image data analysis unit 45 on a display screen.

Note that when the template image is a three-dimensional image of a phantom, the X-ray image to be compared is a projection image in a field-of-view direction. Or, when the template image is a projection image of the whole body, the X-ray image to be compared is a projection image at an angle closest to the representative angle of the projection image of the whole body. Note that a three-dimensional cranial blood vessel X-ray contrast image (a three-dimensional image including bone and blood vessel images) or the like is usable as the three-dimensional image of the phantom. Furthermore, when the generated X-ray image is a non-contrast image, the projection image of the whole body in the template image is a bone projection image. Alternatively, when the generated X-ray image is a contrast image, the projection image of the whole body is a projection image including bone and blood vessel images. Or, when the generated X-ray image is a difference image, the projection image of the whole body is a blood vessel projection image.

Furthermore, "by comparing" may be interpreted as, for example, "by comparing and performing pattern matching". The pattern matching indicates that the map (the above-described template image) of a characteristic structure is held and matching with the structure is performed.

The image data analysis unit 45 may have a function (i) or (ii) of supporting pattern matching by estimating a field-of-view portion and limiting the range of the pattern matching before comparing the template image with the X-ray image.

(i) a function of estimating the positions of the object P and the field of view to estimate a field-of-view portion based on the angle of the C-arm 19, the position of the bed 17, SID (Source-Image Distance), FOV (Field Of View), object (patient) information (height and weight), and object (patient) body posture information which are acquired from the system control unit 25

(ii) a function of estimating a field-of-view portion based on a target portion registered in an imaging program or an examination protocol acquired from the system control unit 25

An exposure dose reduction target portion corresponds to a high sensitivity portion such as an eyeball or thyroid, and an arbitrarily designated portion. As the arbitrarily designated portion, for example, the hand portion of a technician at the time of paracentesis, the hand portion of an assistant at the time of PPI (Percutaneous Peripheral Intervention), or the like is usable, as needed.

For example, the range of an exposure dose reduction target portion in the template image is designated on the template image, or can be designated in other position information (which is structure information for identifying a position on the object or examination room coordinates, and is used by performing alignment with the template image).

Moreover, the image data analysis unit (setting device) 45 may detect a predetermined instrument projected on the X-ray image generated by the image generation unit 28 based on the X-ray image, and set a region of interest including the instrument. For example, the image data analysis unit 45 may include a storage unit (not shown) for storing a template image representing a predetermined instrument, and detect the predetermined instrument from the X-ray image by comparing the X-ray image with the template image. Note that a catheter, an ultrasonic probe, or the like is usable as the predetermined instrument, as needed.

Figure 4:
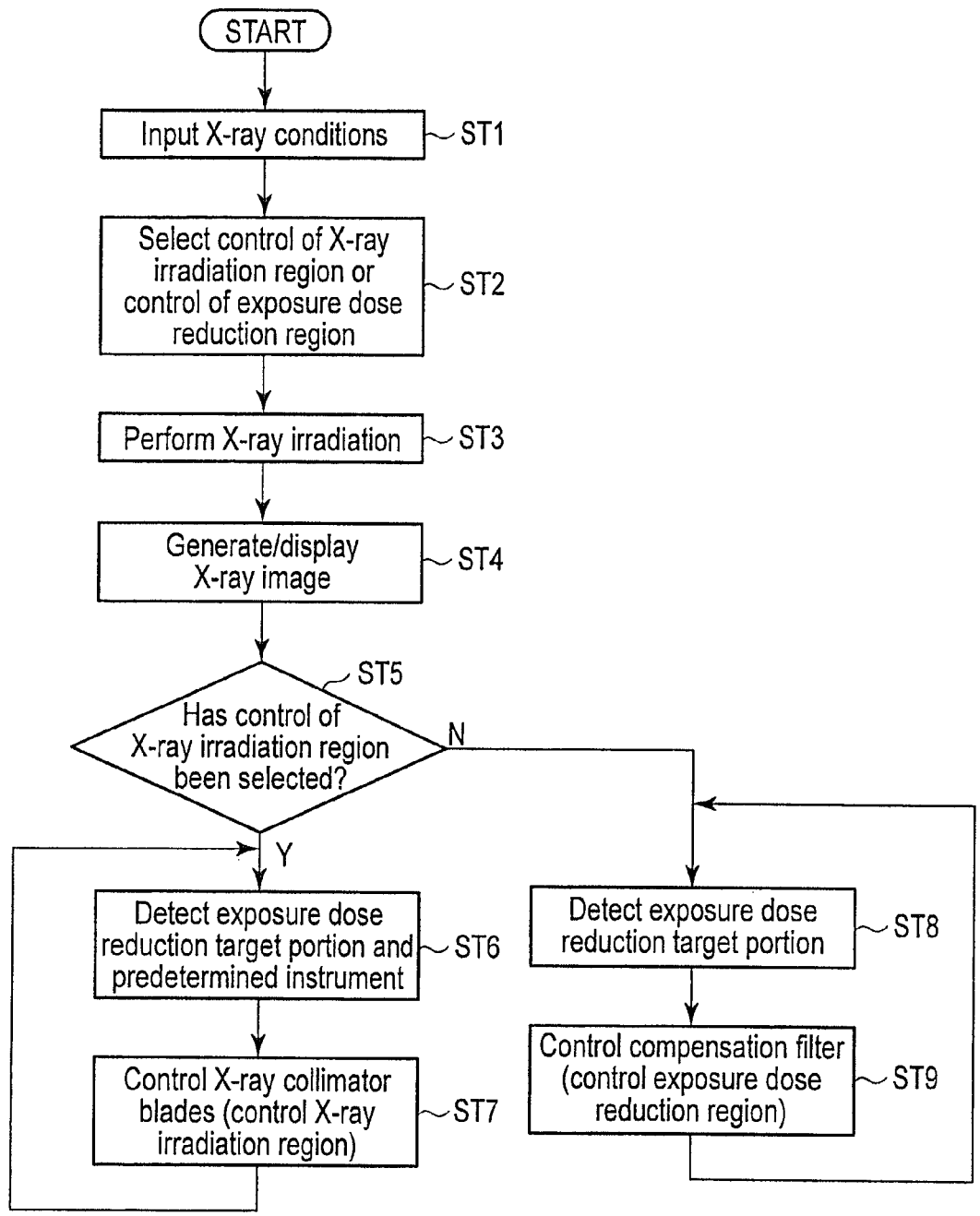
FIG. 4 is a flowchart for explaining an operation according to the first embodiment.

The operation of the X-ray diagnostic apparatus with the above-described arrangement will be described with reference to a flowchart shown in FIG. 4. Note that a fluoroscopy mode whose purpose is to acquire a moving image will be exemplified as imaging. The embodiment, however, is not limited to this. A similar imaging operation is also applicable to an actual imaging mode in which an X-ray irradiation intensity is higher than that in fluoroscopy imaging and whose purpose is to acquire a still image. Alternatively, the image generation unit 28 may generate an X-ray image which includes a moving image inside the X-ray irradiation region R and a still image outside the X-ray irradiation region R. Similarly, the image generation unit 28 may generate an X-ray image which includes a still image inside an exposure dose reduction region r and a moving image outside the exposure dose reduction region r. That is, the image generation unit 28 may generate an X-ray image by combining the current moving image with a still image almost immediately before attenuation by the attenuation device. Alternatively, the image generation unit 28 may generate an X-ray image by combining the current moving image with a still image almost immediately before movement control of the X-ray collimator blades 13*a* to 13*d* or the compensation filters 15*a* and 15*b*. The same goes for each of the following embodiments, too.

After confirming information of the object P (the name of a patient and the like), an operator such as a doctor or technician inputs X-ray conditions (a tube voltage, a tube current, a fluoroscopy time, and the like) appropriate for the object P through the operation unit 27 (step ST1). Note that a tube current for fluoroscopy imaging is generally set smaller than that for actual imaging, and auto brightness control (ABC) controls the X-ray conditions to appropriate ones. The operator selects control of the X-ray irradiation region R or control of the exposure dose reduction region by operating the operation unit 27 (step ST2). This selection operation is not limited to direct designation of "control of the X-ray irradiation region R" or "control of the exposure dose reduction region", and may be indirect selection of "control of the X-ray irradiation region R" by designating "except for brain" as an X-ray irradiation target. Note that if "brain" is designated as an X-ray irradiation target, a wide field of view is necessary, and thus "control of the exposure dose reduction region" is indirectly selected. Furthermore, "control of the X-ray irradiation region R" may be interpreted as "control of the X-ray collimator blades 13a to 13d" and "control of the exposure dose reduction region" may be interpreted as "control of the compensation filters 15a and 15b".

Under the control of the system control unit 25, the X-ray tube 11 irradiates the object P lying on the bed 17 with X-rays via the X-ray controller 29 and the high voltage generator 31 (step ST3). At this stage, the collimator control unit 33 controls the X-ray collimator blades 13a, 13b, 13c, and 13d of the X-ray collimator 13 so that the X-ray irradiation region R becomes largest. Similarly, in order not to attenuate X-ray irradiation, the compensation filter control unit 35 holds the compensation filters 15a and 15b of the compensation filter unit 15 at positions such that the exposure dose reduction region becomes smallest.

An X-ray image is generated and displayed based on X-rays transmitted through the object P (step ST4). That is, the X-ray detector 16 detects the X-rays transmitted through the object P, and converts the X-rays into an electrical signal. This conversion may be direct conversion of converting the X-rays into an electrical signal, or indirect conversion of converting the X-rays into an electrical signal through light. The electrical signal acquired by the X-ray detector 16 undergoes desired image processing, is converted into a TV video signal by the image generation unit 28, and is displayed as an X-ray fluoroscopic image on the image display unit 43.

In accordance with a selection result in step ST2 (step ST5), the image data analysis unit 45 detects an exposure dose reduction target portion and a predetermined instrument from the generated X-ray image.

Figure 5:
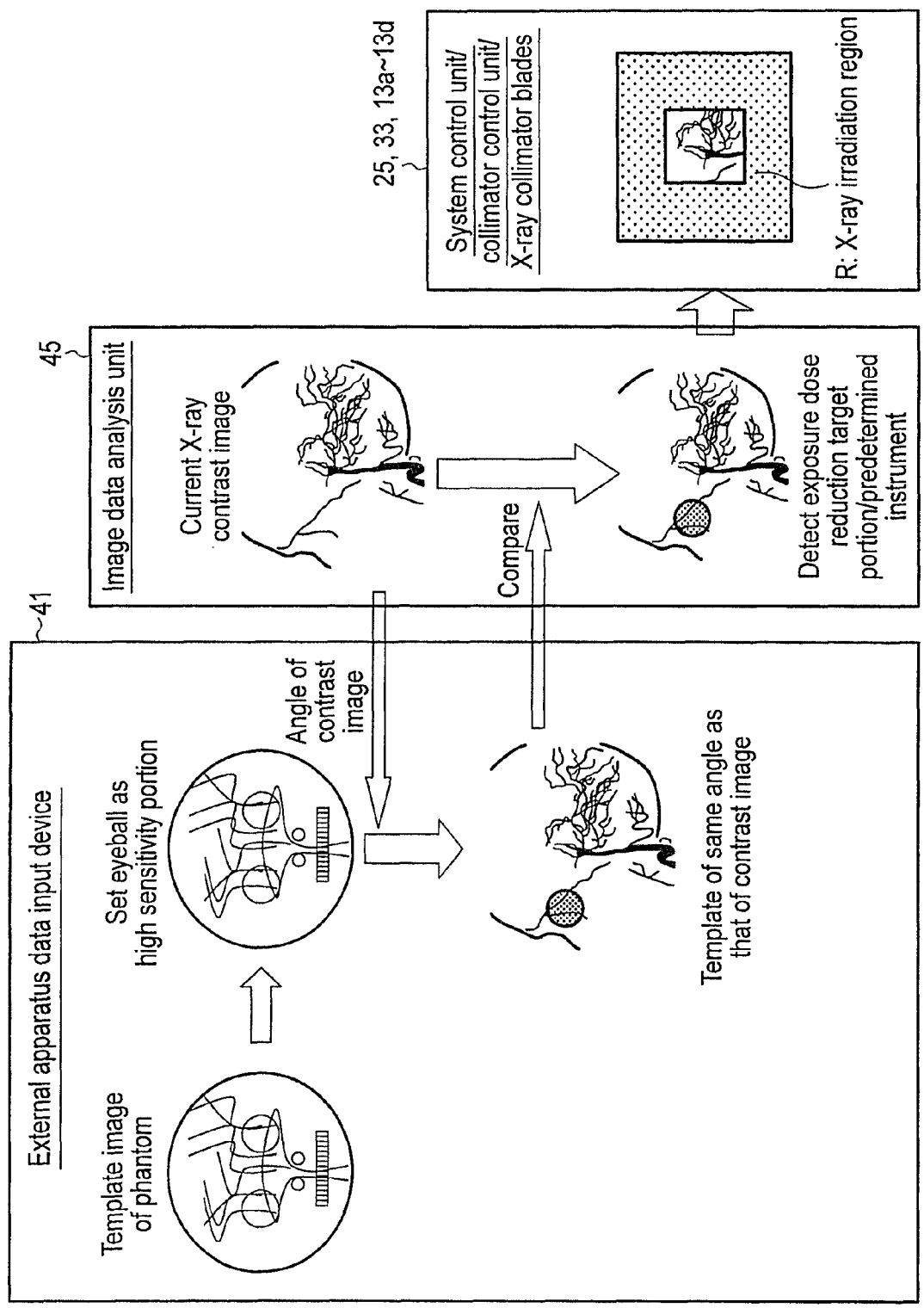
FIG. 5 is a schematic view for explaining the operation according to the first embodiment.

If, for example, control of the X-ray irradiation region R is selected (YES in step ST5), the image data analysis unit 45 detects an exposure dose reduction target portion and a predetermined instrument projected on the X-ray image based on the X-ray image (step ST6), and sets a region of interest including the instrument. More specifically, as shown in FIG. 5, the image data analysis unit 45 sends the angle of the generated X-ray image (current X-ray contrast image) to the external apparatus data input device 41, and acquires, from the external apparatus data input device 41, a template image of the same angle as that of the generated X-ray image, for which a high sensitivity region has been designated in advance. The image data analysis unit 45 compares the acquired template image with the X-ray image generated by the image generation unit 28, and detects an exposure dose reduction target portion and the predetermined instrument projected on the X-ray image by pattern matching of the template image and the X-ray image. Furthermore, the image data analysis unit 45 sends portion region data indicating a region including the detected portion and region-of-interest data indicating the region of interest to the collimator control unit 33 via the system control unit 25.

Note that since the position and size of the exposure dose reduction target portion are different among individuals, the portion region data may indicate a region including an arbitrary margin which can be modified by operating the operation unit 27. If, for example, the X-ray image includes the exposure dose reduction target portion, the portion may be designated on the X-ray image, and the contours of the portion may be drawn by tracing of a cursor or the like, thereby automatically adjusting the margin to have a predetermined width or larger from the contours.

Based on the portion region data and the region-of-interest data, the collimator control unit 33 controls the movement of each of the X-ray collimator blades 13a to 13d to shield the exposure dose reduction target portion from X-rays while irradiating the region of interest including the instrument with the X-rays (step ST7). The X-ray collimator blades 13a to 13d independently move to limit the irradiation region R of the X-rays on the object P to the region of interest. After that, the X-ray diagnostic apparatus 1 repeatedly executes the processing in steps ST6 and ST7.

Figure 6:
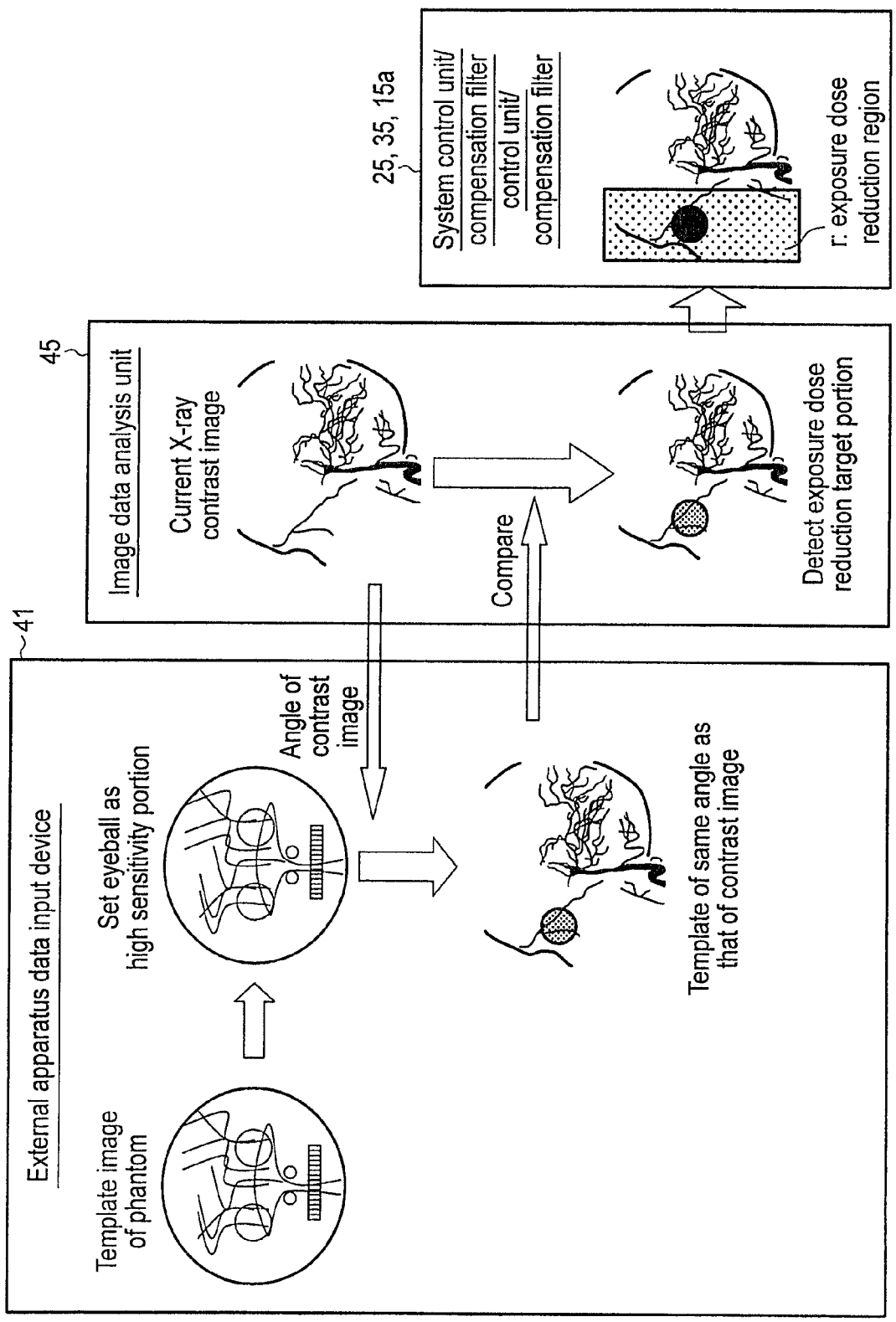
FIG. 6 is a schematic view for explaining the operation according to the first embodiment.

On the other hand, if control of the exposure dose reduction region is selected (NO in step ST5), the image data analysis unit 45 detects an exposure dose reduction target portion based on the X-ray image (step ST8). More specifically, as shown in FIG. 6, the image data analysis unit 45 compares the template image acquired from the external apparatus data input device 41 with the X-ray image generated by the image generation unit 28, and detects an exposure dose reduction target portion by pattern matching of the template image and the X-ray image, as described above. The image data analysis unit 45 sends portion region data indicating a region including the detected portion to the compensation filter control unit 35 via the system control unit 25.

Based on the portion region data, the compensation filter control unit 35 controls the movement of the compensation filter 15a to shield the exposure dose reduction target portion from the X-rays (step ST9). The compensation filter 15a individually moves to attenuate the X-rays to irradiate the exposure dose reduction region r. After that, the X-ray diagnostic apparatus 1 repeatedly executes the processing in steps ST8 and ST9. Note that the X-ray diagnostic apparatus 1 excludes the exposure dose reduction region r from estimation of X-ray conditions (X-ray conditions are controlled based on image information of a portion except for the position of the compensation filter). The same goes for each of the following embodiments, too.

As described above, according to the embodiment, with the arrangement of detecting an exposure dose reduction target portion based on an X-ray image, and attenuating X-rays to irradiate a region including the detected portion, it is possible to automatically reduce the exposure dose of the exposure dose reduction target portion.

In addition, it is possible to detect a high sensitivity portion or an object to be avoided, and the distal end of a catheter currently operated, thereby inserting the compensation filters 15a and 15b to cover the high sensitivity portion. Alternatively, a region of interest of collimator positioning synchronous fluoroscopy (fluoroscopy in which a collimator automatically limits the irradiation region to a designated region of interest) can be set so as to avoid a high sensitivity portion. It is, therefore, possible to reduce the exposure dose of an exposure dose reduction target portion at the time of fluoroscopy/imaging.

Furthermore, with the arrangement of automatically moving the X-ray collimator blades 13a to 13d or the compensation filters 15a and 15b to attenuate X-rays to irradiate a region including an exposure dose reduction target portion without any manual operation, it is possible to reduce the work load of an operator at the time of diagnosis.

Second Embodiment

An X-ray diagnostic apparatus according to the second embodiment will be described next.

This embodiment is a practical example of the first embodiment, in which an X-ray image is a non-contrast image or contrast image of a head which faces front, an exposure dose reduction target portion is an eyeball, and a predetermined instrument is a catheter. Note that an X-ray diagnostic apparatus 1 has the same arrangement as that described in the first embodiment.

In this case, the X-ray diagnostic apparatus 1 executes steps ST1 to ST4, as described above.

In accordance with a selection result in step ST2 (step ST5), an image data analysis unit 45 detects an exposure dose reduction target portion and a predetermined instrument from a generated X-ray image.

Figure 7:
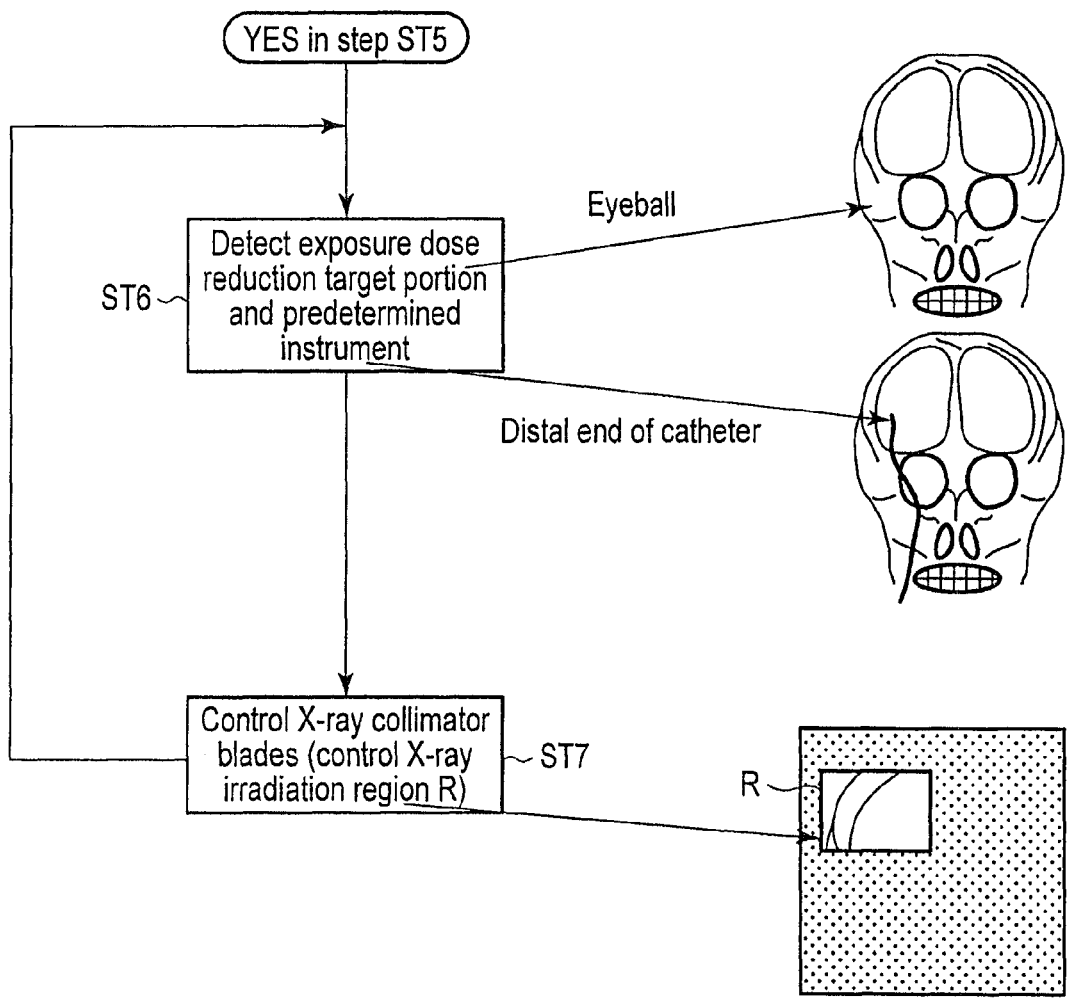
FIG. 7 is a flowchart for explaining the operation of an X-ray diagnostic apparatus according to the second embodiment.

As shown in FIG. 7, for example, if control of an X-ray irradiation region R is selected (YES in step ST5), the image data analysis unit 45 detects an eyeball (exposure dose reduction target portion) and the distal end of a catheter (predetermined instrument) projected on the X-ray image based on the X-ray image (step ST6), and sets a region of interest including the distal end of the catheter. The image data analysis unit 45 also sends portion region data indicating a region including the detected eyeball and region-of-interest data indicating a region of interest to a collimator control unit 33 via a system control unit 25.

Based on the portion region data and the region-of-interest data, the collimator control unit 33 controls the movement of each of X-ray collimator blades 13a to 13d to shield the eyeball from X-rays while irradiating the region of interest including the distal end of the catheter with the X-rays (step ST7). The X-ray collimator blades 13a to 13d independently move to limit the irradiation region R of the X-rays to irradiate an object P to the region of interest. After that, the X-ray diagnostic apparatus 1 repeatedly executes the processing in steps ST6 and ST7.

Figure 8:
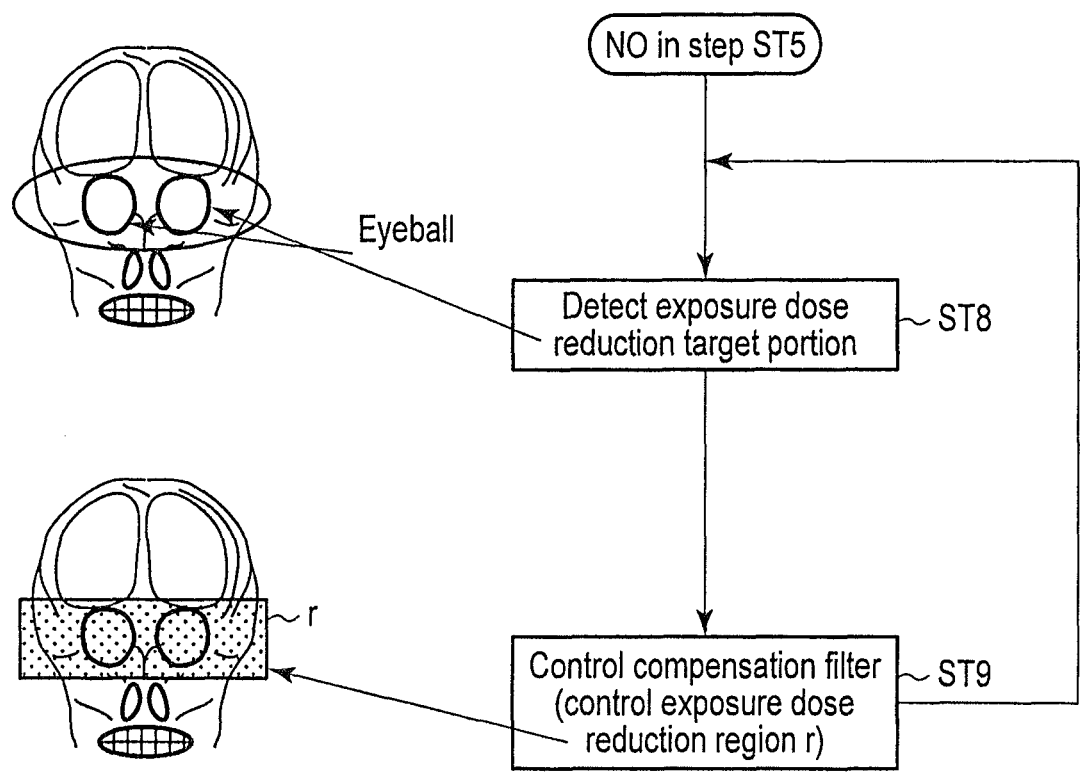
FIG. 8 is a flowchart for explaining the operation according to the second embodiment.

On the other hand, as shown in FIG. 8, if control of an exposure dose reduction region is selected (NO in step ST5), the image data analysis unit 45 detects an eyeball (exposure dose reduction target portion) based on the X-ray image (step ST8). The image data analysis unit 45 sends portion region data indicating a region including the detected eyeball to a compensation filter control unit 35 via the system control unit 25.

Based on the portion region data, the compensation filter control unit 35 controls the movement of a compensation filter 15a to shield the eyeball from the X-rays (step ST9). The compensation filter 15a independently moves to attenuate the X-rays to irradiate an exposure dose reduction region r. After that, the X-ray diagnostic apparatus 1 repeatedly executes the processing in steps ST8 and ST9.

As described above, according to this embodiment, even if the X-ray image is a non-contrast image or contrast image of a head which faces front, the exposure dose reduction target portion is an eyeball, and the predetermined instrument is a catheter, it is possible to obtain the same effects as those in the first embodiment.

Third Embodiment

An X-ray diagnostic apparatus according to the third embodiment will be described next.

This embodiment is another practical example of the first embodiment, in which an X-ray image is a non-contrast image, contrast image, or difference image in PPI (Percutaneous Peripheral Intervention), an exposure dose reduction target portion is the hand of a technician or assistant, and a predetermined instrument is an ultrasonic probe. That is, this embodiment assumes a case in which a clogging of blood vessels is observed using an ultrasonic diagnostic apparatus when a hand/foot is treated. An X-ray diagnostic apparatus 1 has the same arrangement as that described in the first embodiment.

In this case, the X-ray diagnostic apparatus 1 executes steps ST1 to ST4, as described above.

In accordance with a selection result in step ST2 (step ST5), an image data analysis unit 45 detects an exposure dose reduction target portion and a predetermined instrument from a generated X-ray image.

Figure 9:
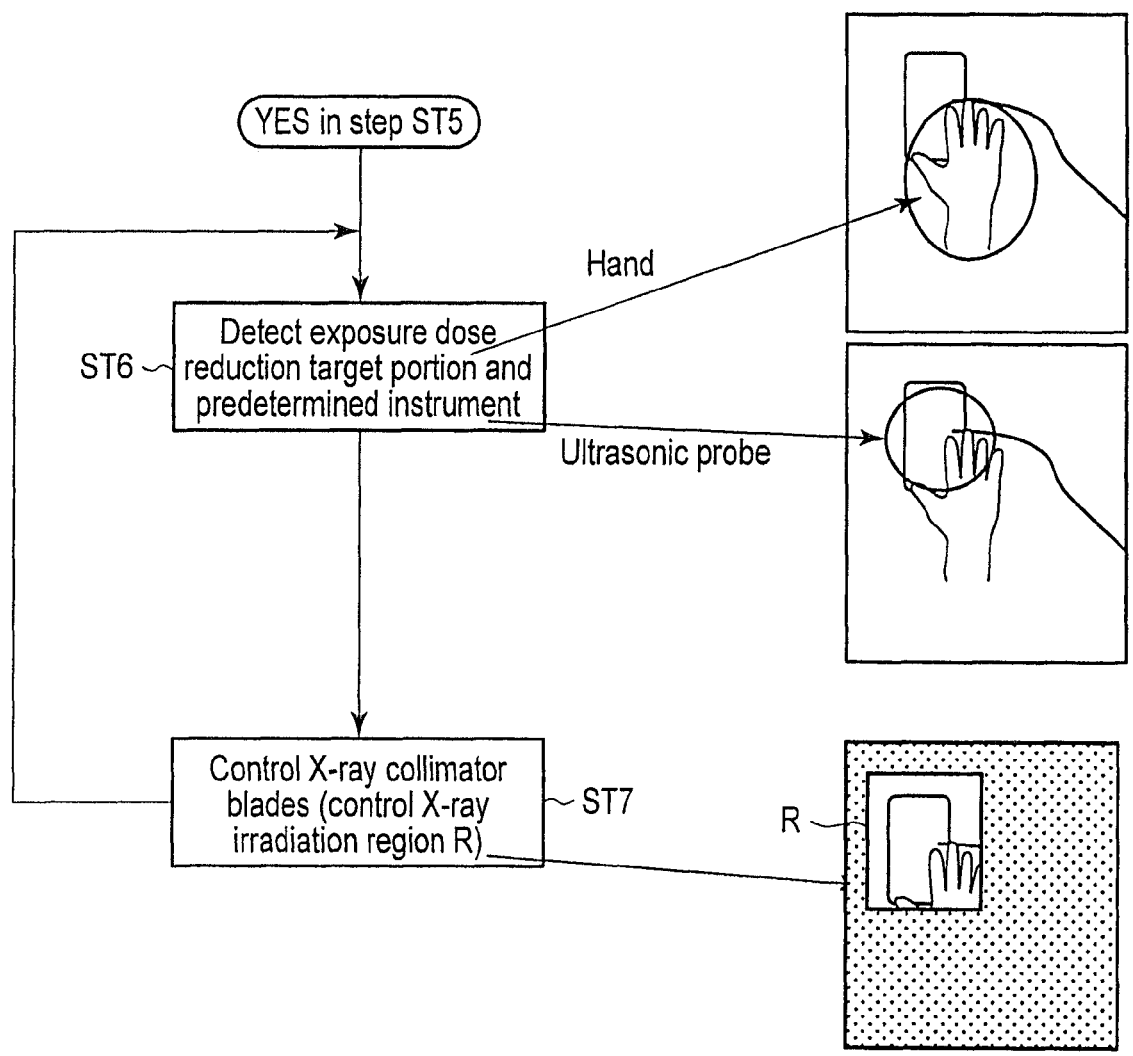
FIG. 9 is a flowchart for explaining the operation of an X-ray diagnostic apparatus according to the third embodiment.

As shown in FIG. 9, for example, if control of an X-ray irradiation region R is selected (YES in step ST5), the image data analysis unit 45 detects a hand (exposure dose reduction target portion) and an ultrasonic probe (predetermined instrument) projected on the X-ray image based on the X-ray image (step ST6), and sets a region of interest including the ultrasonic probe. The image data analysis unit 45 also sends portion region data indicating a region including the detected hand and region-of-interest data indicating a region of interest to a collimator control unit 33 via a system control unit 25.

Based on the portion region data and the region-of-interest data, the collimator control unit 33 controls the movement of each of X-ray collimator blades 13a to 13d to shield the hand from X-rays while irradiating the region of interest including the ultrasonic probe with the X-rays (step ST7). The X-ray collimator blades 13a to 13d independently move to limit the irradiation region R of the X-rays on an object P to the region of interest. After that, the X-ray diagnostic apparatus 1 repeatedly executes the processing in steps ST6 and ST7.

Figure 10:
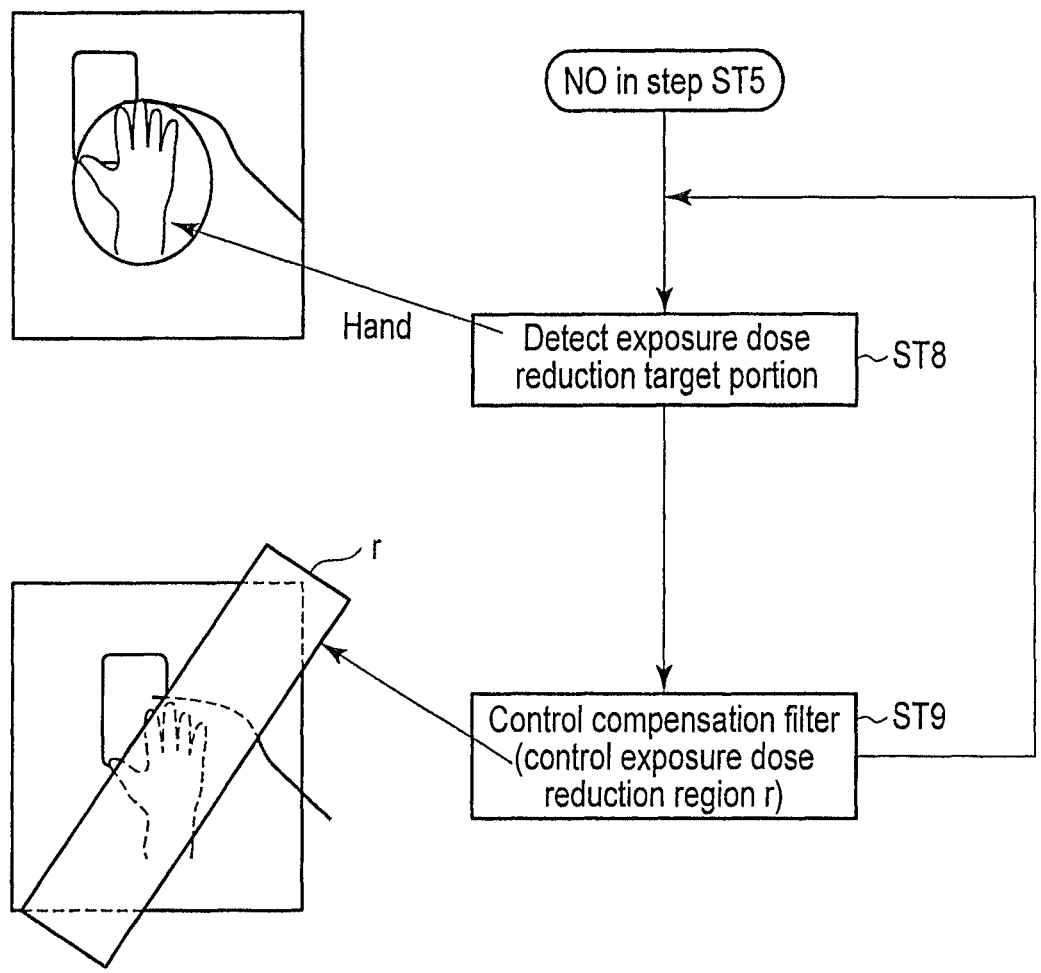
FIG. 10 is a flowchart for explaining the operation according to the third embodiment.

On the other hand, as shown in FIG. 10, if control of an exposure dose reduction region r is selected (NO in step ST5), the image data analysis unit 45 detects a hand (exposure dose reduction target portion) based on the X-ray image (step ST8). The image data analysis unit 45 sends portion region data indicating a region including the detected hand to a compensation filter control unit 35 via the system control unit 25.

Based on the portion region data, the compensation filter control unit 35 controls the movement of a compensation filter 15a to shield the hand from the X-rays (step ST9). The compensation filter 15a independently moves to attenuate the X-rays to irradiate the exposure dose reduction region r. After that, the X-ray diagnostic apparatus 1 repeatedly executes the processing in steps ST8 and ST9.

As described above, according to this embodiment, even if the X-ray image is a non-contrast image, contrast image, or difference image in PPI, the exposure dose reduction target portion is the hand of a technician or assistant, and the predetermined instrument is an ultrasonic probe, it is possible to obtain the same effects as those in the first embodiment.

In addition, according to this embodiment, it is possible to suppress the exposure dose of the hand of a technician at the time of paracentesis or that of the hand of an assistant at the time of PPI (Percutaneous Peripheral Intervention).

According to at least one of the above-described embodiments, with the arrangement of detecting an exposure dose reduction target portion based on an X-ray image, and attenuating X-rays to irradiate a region including the detected portion, it is possible to automatically reduce the exposure dose of the exposure dose reduction target portion.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
   an X-ray generation device which generates X-rays to irradiate an object;
   an X-ray detector which detects X-rays transmitted through the object;
   an image generation device which generates an X-ray image based on the detected X-rays;
   a storage circuit configured to store a three-dimensional template image;
   an acquiring circuit which rotates the three-dimensional template image in a field-of-view direction of the X-ray image, and acquires the rotated three-dimensional template image of an angle identical to that of the X-ray image;
   a display device which displays the X-ray image;
   a portion detection device which detects an exposure dose reduction target portion by comparing the rotated three-dimensional template image with the X-ray image; and
   an attenuation device which attenuates the X-rays to irradiate a region including the detected exposure dose reduction target portion.

2. The X-ray diagnostic apparatus according to claim further comprising
   a controller configured to perform, when the portion detection device detects the detected exposure dose reduction target portion, movement control of the attenuation device for attenuating the X-rays to irradiate the detected exposure dose reduction target portion,
   wherein the X-ray image comprises a composite image, obtained by replacing a portion of an X-ray fluoroscopic image corresponding to the region with an X-ray image substantially immediately before the movement control is performed, as a moving image.

3. The X-ray diagnostic apparatus according to claim 1, further comprising
   a setting device which detects a predetermined instrument projected on the X-ray image, and sets a region of interest including the instrument,
   wherein the attenuation device includes
   a plurality of X-ray collimator blades independently movable to limit an irradiation region of the X-rays to irradiate the object to the region of interest, and
   an X-ray collimator controller which performs movement control of each of the X-ray collimator blades to block the detected exposure dose reduction target portion from the X-rays while irradiating the region of interest with the X-rays.

4. The X-ray diagnostic apparatus according to claim 1, wherein
   the attenuation device which includes
   a movable compensation filter provided to reduce an exposure dose of the detected exposure dose reduction target portion by attenuating the X-rays to irradiate the detected exposure dose reduction target portion, and
   a compensation filter controller which performs movement control of the compensation filter to cover the exposure dose reduction target detected portion from the X-rays.

* * * * *